(12) United States Patent
Vardi et al.

(10) Patent No.: US 6,682,536 B2
(45) Date of Patent: Jan. 27, 2004

(54) GUIDEWIRE INTRODUCER SHEATH

(75) Inventors: Gil M. Vardi, Town & Country, MO (US); Eric Williams, Fairfield, CA (US); Elsa Chavez, Fremont, CA (US); Henry Bourang, Turlock, CA (US); Niyazi U. Beyhan, Santa Clara, CA (US)

(73) Assignee: Advanced Stent Technologies, Inc., Pleasanton, CA (US)

( * ) Notice: Subject to any disclaimer, the term of this patent is extended or adjusted under 35 U.S.C. 154(b) by 33 days.

(21) Appl. No.: 09/816,690

(22) Filed: Mar. 22, 2001

(65) Prior Publication Data

US 2001/0044622 A1 Nov. 22, 2001

Related U.S. Application Data

(63) Continuation-in-part of application No. 09/533,616, filed on Mar. 22, 2000.
(60) Provisional application No. 60/208,399, filed on May 30, 2000.

(51) Int. Cl.$^7$ ............................................. A61M 25/01
(52) U.S. Cl. ...................................................... 606/108
(58) Field of Search ......................... 606/108; 623/1.11; 600/588

(56) References Cited

U.S. PATENT DOCUMENTS

| | | |
|---|---|---|
| 1,596,754 A | 8/1926 | Mochelle |
| 3,872,893 A | 3/1975 | Roberts |
| 4,140,126 A | 2/1979 | Choudhury |
| 4,410,476 A | 10/1983 | Redding et al. |
| 4,413,989 A | 11/1983 | Schjeldahl |
| 4,421,810 A | 12/1983 | Rasmussen |
| 4,503,569 A | 3/1985 | Dotter |
| 4,552,554 A * | 11/1985 | Gould et al. ................ 604/104 |

(List continued on next page.)

FOREIGN PATENT DOCUMENTS

| | | |
|---|---|---|
| DE | 29701758 U1 | 5/1997 |
| EP | 0804907 A2 | 11/1997 |
| EP | 0876805 A2 | 11/1998 |
| EP | 1031328 A1 | 8/2000 |
| EP | 1031330 A2 | 8/2000 |
| FR | 2678508 A1 | 1/1993 |

(List continued on next page.)

OTHER PUBLICATIONS

SCIMED Life Systems, Inc.—TRIO 14 PTCA catheter, Re-engineering Over-the-Wire Balloon Technology, Company Brochure, 1994.
Caputo et al., "Stent Jail: A Minimum–Security Prison" The American Journal of Cardiology, (1996) 7:1226–1230.
Fischman et al. "A Randomized Comparison of Coronary–Stent Placement and Balloon Angioplasty in the Treatment of Coronary Artery Disease" The New England Journal of Medicine (1994) 331(8): 496–501.
Nakamura et al. "Techniques for Palmaz–Schatz Stent Deployment in Lesions with a Large Side Branch" Catheterization and Cardiovascular Diagnosis (1995) 34:353–361.

(List continued on next page.)

*Primary Examiner*—Ismael Izaguirre
(74) *Attorney, Agent, or Firm*—Patton Boggs LLP

(57) ABSTRACT

Systems and methods for positioning a first guidewire (25) in a primary vessel (M) and a second guidewire (27) in a branch vessel (B). One embodiment comprises an introducer (10) having first (12) and second lumens (14) adapted to slidably receive the first guidewire within the first lumen and the second guidewire within the second lumen. One method embodiment includes inserting the first guidewire into the main vessel, introducing the introducer over the first guidewire, and inserting the second guidewire within the second lumen such that the second guidewire extends into the branch vessel. The introducer is withdrawn while maintaining the first and second guidewires in the respective vessels.

21 Claims, 16 Drawing Sheets

U.S. PATENT DOCUMENTS

| | | |
|---|---|---|
| 4,681,570 A | 7/1987 | Dalton |
| 4,689,174 A | 8/1987 | Lupke |
| 4,733,665 A | 3/1988 | Palmaz |
| 4,739,762 A | 4/1988 | Palmaz |
| 4,759,748 A | 7/1988 | Reed |
| 4,769,029 A | 9/1988 | Patel |
| 4,872,874 A | 10/1989 | Taheri |
| 4,900,314 A | 2/1990 | Quackenbush |
| 4,957,501 A | 9/1990 | Lahille et al. |
| 4,957,508 A | 9/1990 | Kaneko et al. |
| 4,994,071 A | 2/1991 | MacGregor |
| 5,042,976 A | 8/1991 | Ishitsu et al. |
| 5,054,501 A | 10/1991 | Chuttani et al. |
| 5,061,240 A | 10/1991 | Cherian |
| 5,064,435 A | 11/1991 | Porter |
| 5,102,403 A | 4/1992 | Alt |
| 5,104,404 A | 4/1992 | Wolff |
| 5,117,831 A | 6/1992 | Jang |
| 5,122,125 A | 6/1992 | Deuss |
| 5,147,317 A | 9/1992 | Shank et al. |
| 5,217,440 A | 6/1993 | Frassica |
| 5,244,619 A | 9/1993 | Burnham |
| 5,263,932 A | 11/1993 | Jang |
| 5,282,472 A | 2/1994 | Companion et al. |
| 5,304,220 A | 4/1994 | Maginot |
| 5,337,733 A | 8/1994 | Bauerfeind et al. |
| 5,342,297 A | 8/1994 | Jang |
| 5,387,235 A | 2/1995 | Chuter |
| 5,404,887 A | 4/1995 | Prather |
| 5,409,458 A | 4/1995 | Khairkhahan et al. |
| 5,413,586 A | 5/1995 | Dibie et al. |
| 5,417,208 A | 5/1995 | Winkler |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,712 A | 10/1995 | Maginot |
| 5,458,605 A * | 10/1995 | Klemm ................ 604/104 |
| 5,462,530 A | 10/1995 | Jang |
| 5,489,271 A * | 2/1996 | Andersen ............ 604/103.04 |
| 5,489,295 A | 2/1996 | Piplani et al. |
| 5,496,292 A | 3/1996 | Burnham |
| 5,507,769 A | 4/1996 | Marin et al. |
| 5,522,801 A | 6/1996 | Wang |
| 5,531,788 A | 7/1996 | Dibie et al. |
| 5,545,132 A | 8/1996 | Fagan et al. |
| 5,562,724 A | 10/1996 | Vorwerk et al. |
| 5,562,725 A | 10/1996 | Schmitt et al. |
| 5,575,818 A | 11/1996 | Pinchuk |
| 5,593,442 A | 1/1997 | Klein |
| 5,607,444 A | 3/1997 | Lam |
| 5,609,627 A | 3/1997 | Goicoechea et al. |
| 5,613,980 A | 3/1997 | Chauhan ................ 606/194 |
| 5,613,981 A | 3/1997 | Boyle et al. |
| 5,617,878 A | 4/1997 | Taheri |
| 5,628,788 A | 5/1997 | Pinchuk |
| 5,632,763 A | 5/1997 | Glastra |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,693,084 A | 12/1997 | Chutter |
| 5,693,086 A | 12/1997 | Goicoechea et al. |
| 5,707,354 A | 1/1998 | Salmon et al. |
| 5,709,713 A | 1/1998 | Evan et al. |
| 5,716,365 A | 2/1998 | Goicoechea et al. |
| 5,718,724 A | 2/1998 | Goicoechea et al. |
| 5,720,735 A | 2/1998 | Dorros |
| 5,723,004 A | 3/1998 | Dereume et al. |
| 5,733,303 A | 3/1998 | Israel et al. |
| 5,749,825 A | 5/1998 | Fischell et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,800,508 A | 9/1998 | Goicoechea et al. |
| 5,824,036 A | 10/1998 | Lauterjung |
| 5,824,040 A | 10/1998 | Cox et al. |
| 5,824,044 A | 10/1998 | Quiachon et al. |
| 5,827,320 A | 10/1998 | Richter et al. |
| 5,836,966 A | 11/1998 | St. Germain |
| 5,843,031 A | 12/1998 | Hermann et al. ............. 604/95 |
| 5,851,210 A | 12/1998 | Torossian |
| 5,851,464 A | 12/1998 | Davila et al. |
| 5,865,178 A | 2/1999 | Yock |
| 5,868,777 A | 2/1999 | Lam |
| 5,897,588 A | 4/1999 | Hull et al. |
| 5,906,640 A | 5/1999 | Penn et al. |
| 5,913,895 A | 6/1999 | Burpee et al. |
| 5,913,897 A | 6/1999 | Corso, Jr. et al. |
| 5,922,020 A | 7/1999 | Klein et al. |
| 5,938,682 A | 8/1999 | Hojeibane |
| 5,961,548 A | 10/1999 | Shmulewitz |
| 5,972,018 A | 10/1999 | Israel et al. |
| 6,013,091 A | 1/2000 | Ley et al. |
| 6,017,363 A | 1/2000 | Hojeibane |
| 6,030,414 A | 2/2000 | Taheri |
| 6,033,434 A | 3/2000 | Borghi |
| 6,036,682 A | 3/2000 | Lange et al. |
| 6,039,749 A | 3/2000 | Marin et al. |
| 6,048,361 A | 4/2000 | VanOepen |
| 6,096,073 A | 8/2000 | Webster et al. |
| 6,099,497 A | 8/2000 | Adams et al. |
| 6,129,738 A | 10/2000 | Lashinski et al. |
| 6,165,195 A | 12/2000 | Wilson et al. |
| 6,217,527 B1 * | 4/2001 | Selmon et al. ............. 600/585 |
| 6,221,080 B1 * | 4/2001 | Power ................ 606/108 |
| 6,231,563 B1 * | 5/2001 | White et al. ................ 604/284 |
| 6,387,120 B2 | 5/2002 | Wilson et al. |
| 6,475,208 B2 | 11/2002 | Mauch |
| 2002/0111675 A1 | 8/2002 | Wilson |

FOREIGN PATENT DOCUMENTS

| | | |
|---|---|---|
| WO | WO 88/06026 A2 | 8/1988 |
| WO | WO 92/19308 A1 | 11/1992 |
| WO | WO 96/41592 A1 | 12/1996 |
| WO | WO 97/33532 A2 | 9/1997 |
| WO | WO 97/45073 A1 | 12/1997 |
| WO | WO 98/17204 | 4/1998 |
| WO | WO 98/35634 | 8/1998 |
| WO | WO 98/44871 | 10/1998 |
| WO | WO 98/48733 | 11/1998 |
| WO | WO 98/52497 | 11/1998 |
| WO | WO 99/17680 | 4/1999 |
| WO | WO 99/39661 | 8/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 A1 | 9/2000 |

OTHER PUBLICATIONS

Serruys et al. "A comparison of balloon–expandable stent implantation with balloon angioplasty in patients with coronary artery disease" The New England Journal of Medicine (1994) 331(8): 489–495.

Colombo et al. "Kissing' Stents for Birucational Coronary Lesion" Catheterization and Cardiovascular Diagnosis, (1993) 30:327–330.

Carrie et al. "'T' shaped stent placement: A technique for the treatment of dissected bifurcation lesions" Catheterization and cardiovascular diagnosis, (1996) 37:311–313.

Katoh et al. "New Double Wire Technique to Stent Ostial Lesions" Catheterization and Cardiovascular Diagnosis, (1997) 40: 400–402.

Lewis et al. "Acute Procedural Results in the Treatment of 30 Coronary Artery Bifurcation Lesions with a Double–Wire Atherectomy Technique for Side Branch Protection", American Heart Journal (1994) 127:1600–1607.

* cited by examiner

GUIDEWIRE INTRODUCER SHEATH

CROSS-REFERENCE TO RELATED APPLICATIONS

The present invention is related to and claims the priority and benefit of the following U.S. patent applications, the complete disclosures of which are incorporated herein by reference:

application Ser. No. 09/533,616 filed Mar. 22, 2000; and

Provisional Patent Application No. 60/208,399, filed May 30, 2000.

Further related cases, whose disclosures are incorporated herein by reference, include U.S. patent application Ser. No. 08/744,022 filed Nov. 4, 1996, now abandoned; Ser. No. 08/935,383 filed Sep. 23, 1997; Ser. No. 09/007,265 filed Jan. 14, 1998; Ser. No. 09/325,996 filed Jun. 4, 1999, Ser. No. 09/455,299 filed Dec. 6, 1999; No. 60/088,301 filed Jun. 5, 1998; and PCT Patent Application No. PCT/US99/00835 filed Jan. 14, 1999.

TECHNICAL FIELD

The present invention relates to systems and methods for positioning guidewires in a body lumen, and to catheter systems for delivering stents.

BACKGROUND OF THE INVENTION

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al., *New England Journal of Medicine* 331: 489–495 (1994) and Fischman, D L et al. *New England Journal of Medicine* 331:496–501 (1994)). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the main vessel and/or its branches, or the bifurcation point and also limits the ability to insert a branch stent into the side branch if the result of treatment of the main, or main, vessel is suboptimal. Suboptimal results may occur as a result of several mechanisms, such as displacing diseased tissue, plaque shifting, vessel spasm, dissection with or without intimal flaps, thrombosis, and embolism.

As described in related copending U.S. patent application Ser. No. 08/744022 filed Nov. 4, 1996, now abandoned; Ser. No. 09/007265 filed Jan. 14, 1998; Ser. No. 08/935,383 filed Sep. 23, 1997; and No. 60/088301 filed Jun. 5, 1998; and PCT Patent Application Publication No. WO 99/00835 filed Jan. 14, 1998; systems have been developed for deploying a main stent in a main vessel at the intersection of a main vessel and a branch vessel with a branch stent extending into a branch vessel through a side opening in the main stent.

In a first approach, these systems describe first inserting a first guidewire, then inserting a second guidewire and then inserting main and branch stents over the respective first and second guidewires and into the bifurcation, wherein the second guidewire passes through a side hole in the main stent and into the branch vessel. In a second approach, these systems describe inserting a first guidewire, then inserting an assembly (comprising the main stent and a system for positioning the second guidewire, for example, a dual lumen catheter) over the first guidewire and into the bifurcation. Thereafter, the second guidewire is fed through its positioning system such that the second guidewire passes out through the side opening in the main stent, and into the branch vessel.

Unfortunately, several difficulties exist in the first approach when attempting to first insert separate guidewires into both the main vessel and the secondary vessel before positioning the main stent in the main vessel with a or without a branch stent projecting through a side opening in the main stent into a branch vessel.

Specifically, when attempting to guide two such separate guidewires through the main vessel such that one enters the branch vessel, the two guidewires typically tend to wrap around one another and become entangled. Additionally, time and effort is required to individually position each of the two guidewires one after another.

An additional disadvantage of conventional stents is the difficulty in visualizing the stents during and after deployment, and in general, the fact that they are not readily imaged by low-cost and easy methods, such as x-ray or ultrasound imaging.

SUMMARY OF THE INVENTION

The present invention comprises a dual lumen guidewire introducer system for introducing guidewires into main and branch vessels at a bifurcation. The dual lumens of the present guidewire introducer system each have distal openings which are disposed at different locations along the length of the introducer. Specifically, the distal end of the first lumen opening is preferably disposed at the distal end of the introducer, and the distal end of the second lumen opening is preferably disposed at some distance from the distal end of the introducer. As such, the distal end of the first lumen opening is disposed distally to the distal end of the second lumen opening. According, the distal end of the second guidewire protrudes out of the introducer at a location which is proximal to the location at which the distal end of the first guidewire protrudes out of the introducer. A guidewire is received through each of the first and second lumens.

As will be explained, an advantage of the present dual lumen catheter system is that it may be used to position a first guidewire in a main vessel and a second guidewire into a branch vessel such that either: (1) a main stent may be deployed in a main vessel and a branch stent in a branch vessel, with the branch stent being deployed through an opening in the side of the primary stent with the side opening being in registry with the ostium of the branch vessel, or (2) a main stent may be deployed in a main vessel with a side opening in the main stent being positioned in registry with the ostium of the branch vessel. Alternative main and/or branch stent positioning procedures may also be employed after the system of the present invention has positioned the first and second guidewires in the respective main and branch vessels. The present system may be used in conjunction with any of a variety of existing stenting systems, including "kissing" or "hugging" balloon and stent systems.

It is to be understood that the used of the present invention are not limited to stent placement. Instead, the present system may in fact be used for any surgical application is which it is beneficial to position first and second guidewires into different branches of a vessel bifurcation.

An important advantage of the present dual lumen guidewire introduction catheter system is that it avoids having to separately position first and second guidewires within the respective main and branch vessels one at a time. As such, the potential for the first and second guidewires tangling around one another is avoided. For example, the present system may be used for the deployment of distal protection devices, "kissing" balloon techniques, and renal stenting where one wire is positioned proximal to the renal and a second wire is parked in the renal vessel. The first wire is used to either deliver a stent or protection device proximal to the renal and the second wire is used to deliver a stent or other device, for example, an ultrasound system.

Rather, with the present invention, only a single guidewire needs to initially be placed within the main vessel, with the present guidewire introducer system subsequently facilitating positioning of the second guidewire in the branch vessel. Having dual lumens which separate the first and second guidewires, the present guidewire system advantageously prevents tangling of the guidewires as they are inserted into the bifurcation.

In preferred aspects, a radiopaque marker is provided at the distal end opening of the second lumen, such that the location at which the distal end of the second guidewire protrudes out of the introducer can be viewed under fluoroscopy. Optionally, a radiopaque marker may also be provided at the distal end opening of the first lumen, such that the surgeon can determine that he has advanced distally past the bifurcation.

In optional preferred aspects, radiopaque markers are provided on opposite sides of the introducer shaft at a location proximal the distal end of the second lumen. Such radiopaque markers may be advantageously used to assist the surgeon in aligning a side opening in a main stent with the ostium of a branch vessel.

In optional preferred aspects of the invention, a balloon is positioned at the distal end of the guidewire introducer system. Such balloon may be advantageously used to pre-dilate the main vessel of the vessel bifurcation. This is particularly useful when compressing plaque on the vessel walls or otherwise pre-treating the vessel.

The present invention also comprises a method of inserting a main guidewire into a main vessel and a branch guidewire into a branch vessel at an intersection of a main and branch vessel, comprising: (a) advancing a first guidewire through a main vessel such that a distal end of the first guidewire is positioned past (or alternately, proximate to) the intersection of the main and branch vessels; (b) advancing a dual lumen guidewire introducer through the main vessel over the first guidewire, the first guidewire being received within the first lumen of the dual lumen guidewire introducer; (c) positioning the dual lumen guidewire introducer such that the distal end of the first lumen is disposed past the intersection of the main and branch vessels, and such that the distal end of the second lumen is disposed at the intersection of the main and branch vessels; and (d) advancing a second guidewire through the second lumen such that a distal end of the second guidewire passes out of the distal opening of the second lumen and into the branch vessel.

In optional aspects of the preferred method, a balloon positioned at the distal end of the guidewire introducer is inflated to pre-dilate the main vessel. The inflation of the balloon may preferably carried out either before, after or concurrently with, the insertion of the second guidewire into the branch vessel.

In preferred aspects of the method, positioning the dual lumen guidewire introducer such that the distal end of the second lumen is disposed at the intersection of the main and branch vessels comprises viewing a radiopaque marker positioned adjacent to the distal end of the second lumen. Also in preferred aspects of the method, positioning the dual lumen guidewire introducer such that the distal opening of the first lumen is disposed distally past the intersection of the main and branch vessels comprises viewing a radiopaque marker positioned adjacent to the distal end of the second lumen.

In an optional preferred aspect of the present invention, the guidewire introducer is easily removed leaving the first and second guidewires in place in the main and branch vessels. As described in related copending U.S. patent application Ser. No. 08/744,022 filed Nov. 4, 1996, now abandoned; Ser. No. 09/007,265 filed Jan. 14, 1998; Ser. No. 08/935,383 filed Sep. 23, 1997; U.S. Provisional Patent Application No. 60/088,301 filed Jun. 5, 1998; and PCT Patent Application Publication No. WO 99/00835 filed Jan. 14, 1998; first and second catheters may then be advanced over the respective first and second guidewires to position respective main and branch stents.

In further preferred aspects of the present invention, the guidewire introducer is formed of a tear-away material, having longitudinal sections separated by tear-apart seals such that an operator can hold the guidewires while removing the introducer, yet avoid pulling the guidewires out as the introducer is removed.

Further advantages of the present peel away system include the fact that it avoids the need for long exchange length guidewire, since the surgeon is able to access the guidewires at a location much closer to the surface of the patient's body.

Applications of the present system include the cardiac, coronary, renal, peripheral vascular, gastrointestinal, pulmonary, urinary and neurovascular systems and the brain. Further advantages of the present dual lumen catheter system are that it provides an improved stent delivery apparatus, which may deliver primary and branch stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a primary stent is implanted; 4) treat bifurcation lesions in a bifurcated vessel where the branch vessel extends from the side of the primary vessel; and 5) be marked with, or at least partly constructed of, material which is imageable by commonly used intraluminal catheterization visualization techniques including but not limited to ultrasound or x-ray.

DESCRIPTION OF THE SPECIFIC EMBODIMENTS

The present invention provides a dual lumen guidewire introducer and methods of use for the dual lumen guidewire introducer for introducing guidewires into main and branch vessels at a vessel bifurcation. As such, the present invention enables the positioning of guidewires such that main and branch stents can be deployed in the vessel bifurcation after the guidewire introducer has been removed. Alternatively, a main stent can be positioned such that a side opening in the stent is positioned in registry with the ostium of a branch vessel.

Figure 1A:
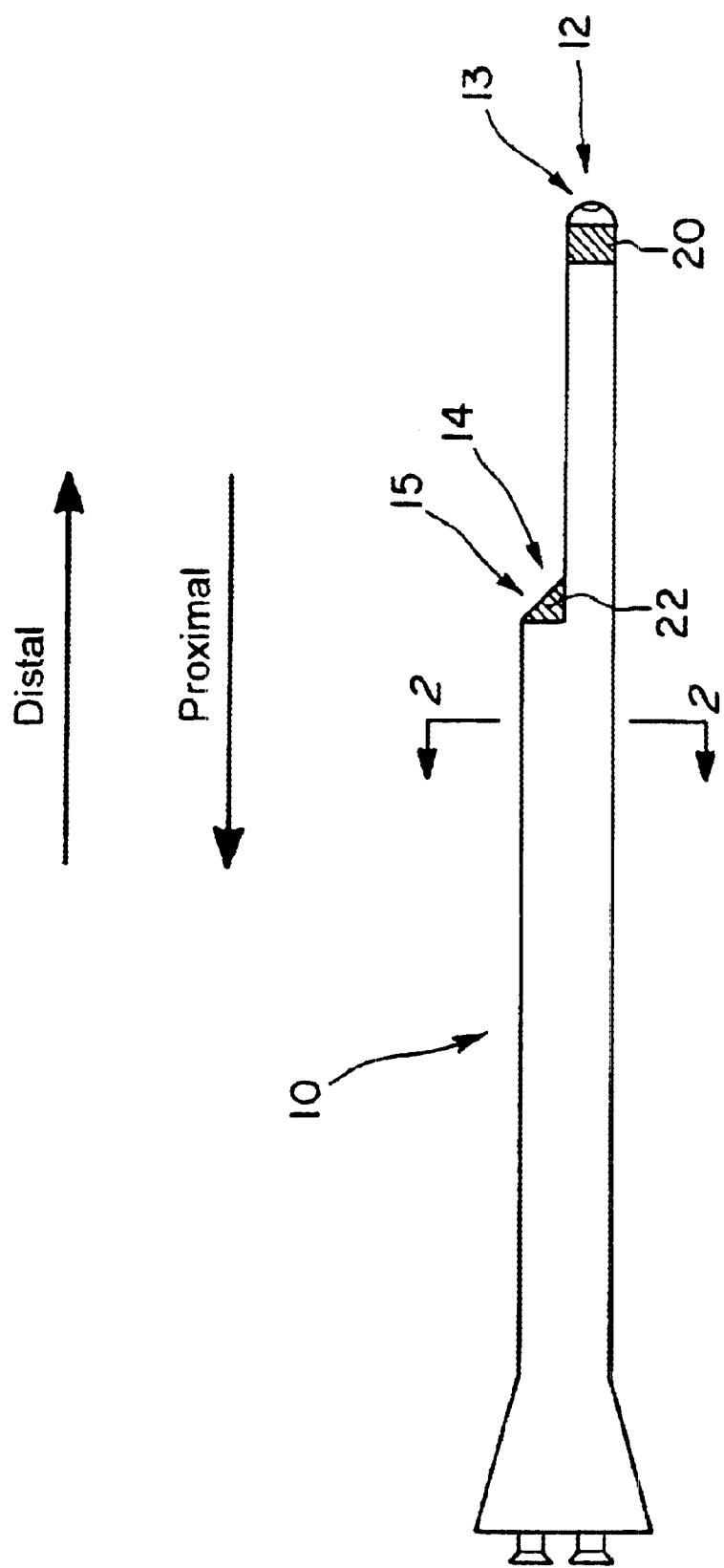
FIG. 1A is an illustration of a dual lumen guidewire introducer.
Figure 1B:
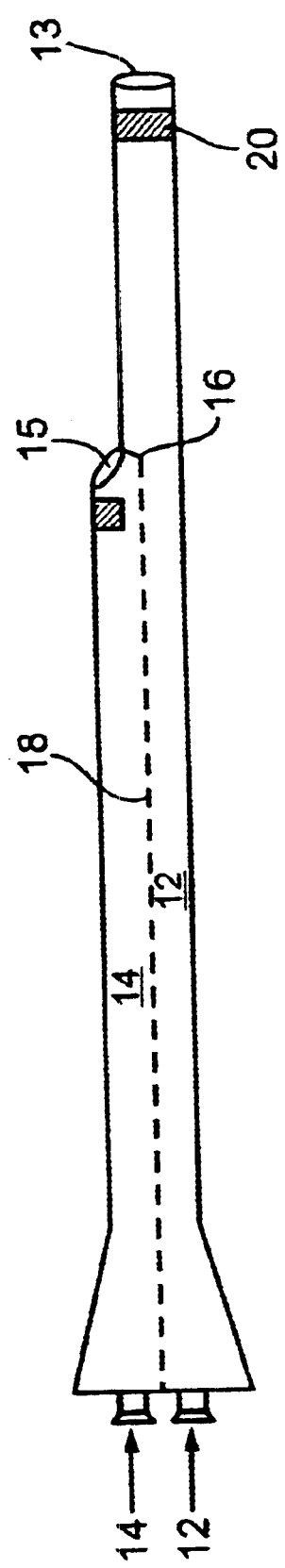
FIG. 1B is an illustration of an alternative embodiment of a dual lumen guidewire introducer according to the present invention.
Figure 2:
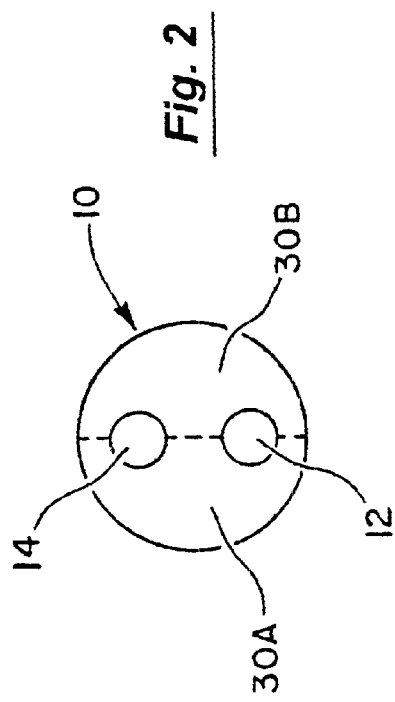
FIG. 2 is a sectional view of the system of FIG. 1A, taken along line 2—2.

Referring first to FIGS. 1 and 2, a guidewire introducer 10 is provided. Guidewire introducer 10 has two lumens 12 and 14 passing therethrough. As can be seen, lumen 12 has a distal end opening 13 which is preferably disposed at the distal end of the introducer. Lumen 14 has a distal end opening 15 which is preferably disposed at a location some distance from the distal end of the introducer.

As will be explained in conjunction with the preferred method, a first guidewire 25 is received through lumen 12 and a second guidewire 27 is received through lumen 14.

A radiopaque marker 20 is optionally disposed adjacent lumen 12 distal end opening 13, and another radiopaque marker 22 is optionally disposed adjacent lumen 14 distal end opening 15. It will be appreciated by those skilled in the art that additional markers 20, 22 also may be used in accordance with the present invention.

In one embodiment, introducer 10 further includes a deflector 16 located near distal opening 15. Deflector 16 may comprise a portion of a seam 18 between lumens 12 and 14. Alternatively, deflector 16 comprise an angled structure made from the same, similar, or different components as lumens 12, 14. Deflector 16 facilitates the diversion of a guidewire tip out of distal opening 15 in a desired direction. In one embodiment, deflector 16 is positioned at a non-parallel angle relative to a longitudinal axis of said lumen 14. In a particular embodiment, the non-parallel angle is about forty-five (45) degrees, although the angle may vary within the scope of the present invention. Deflector 16 may have a flat or a curved surface to deflect the guidewire end.

In one embodiment, distal opening 15 also is positioned at a non-parallel angle relative to the lumen 14 longitudinal axis, which in a particular embodiment is about forty-five (45) degrees. In one embodiment, deflector 16 and distal opening 15 are positioned at about a ninety (90) degree angle relative to one another.

As further discussed herein, in one embodiment, a branch vessel guidewire is fed through lumen 14 and into a branch vessel. The distal tip of the branch vessel guidewire may, or may not, contact deflector 16 and is directed out opening 15 towards the branch vessel.

Figure 3:
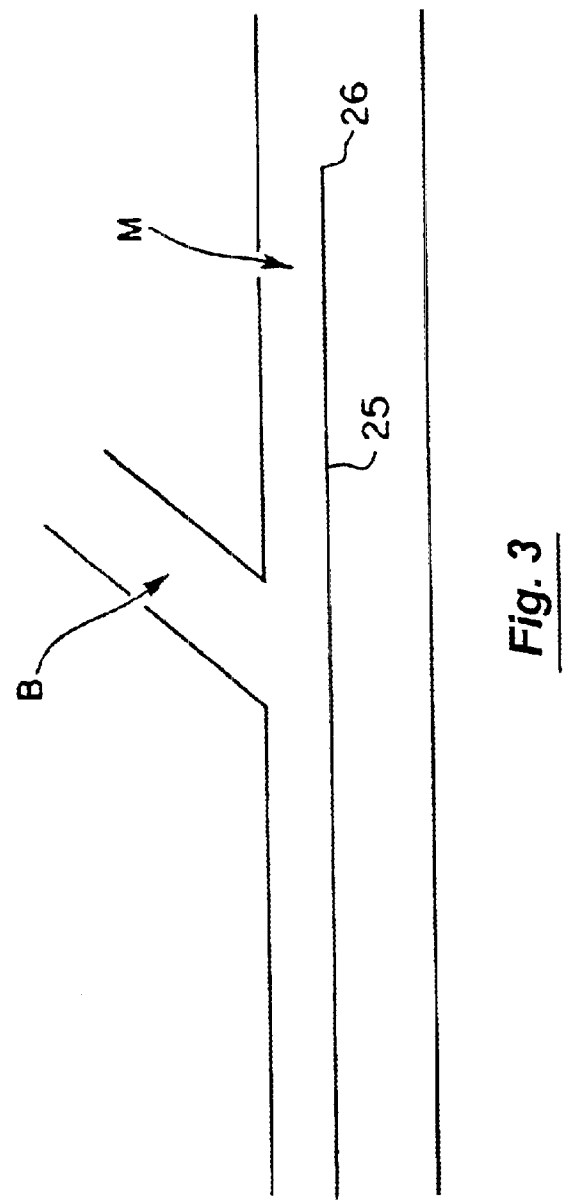
FIG. 3 is an illustration of a placement of first guidewire within a main vessel.
Figure 4:
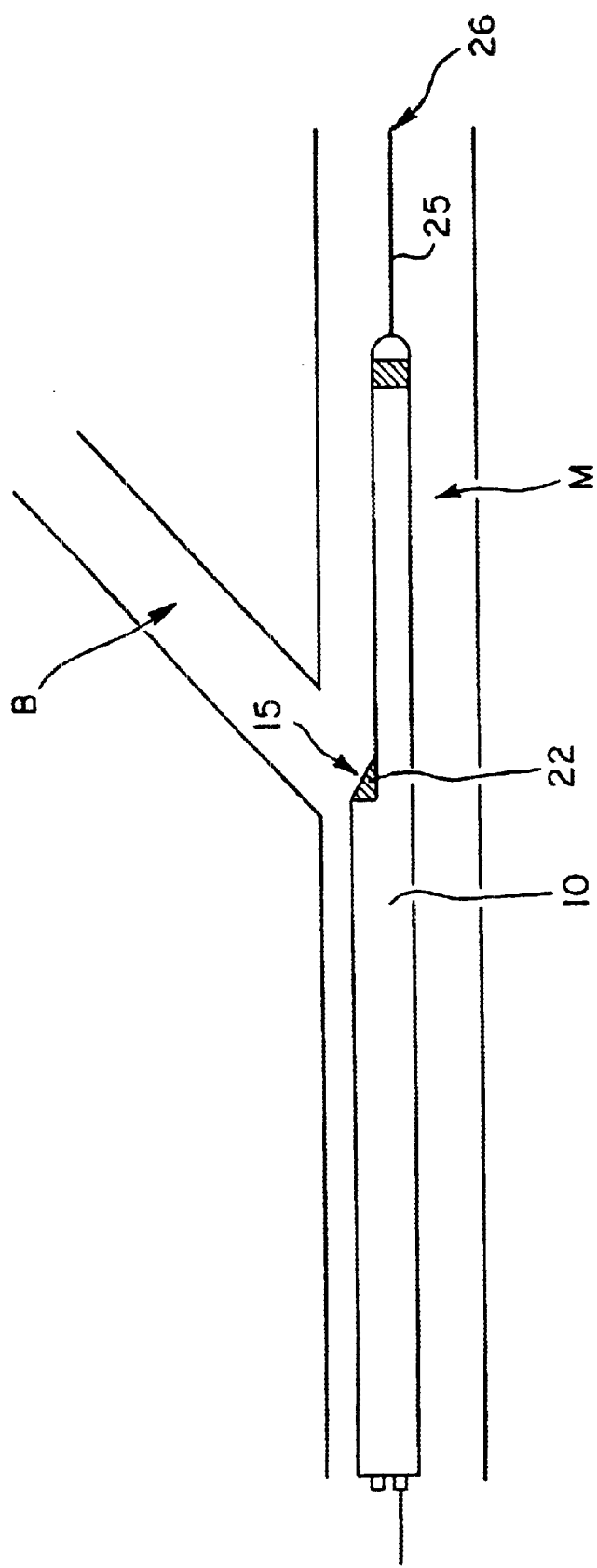
FIG. 4 is an illustration of the present dual lumen guidewire introducer advanced over the first guidewire to a position where the distal end opening of the second lumen is positioned in a vessel bifurcation, adjacent a mouth of the branch vessel.
Figure 5:
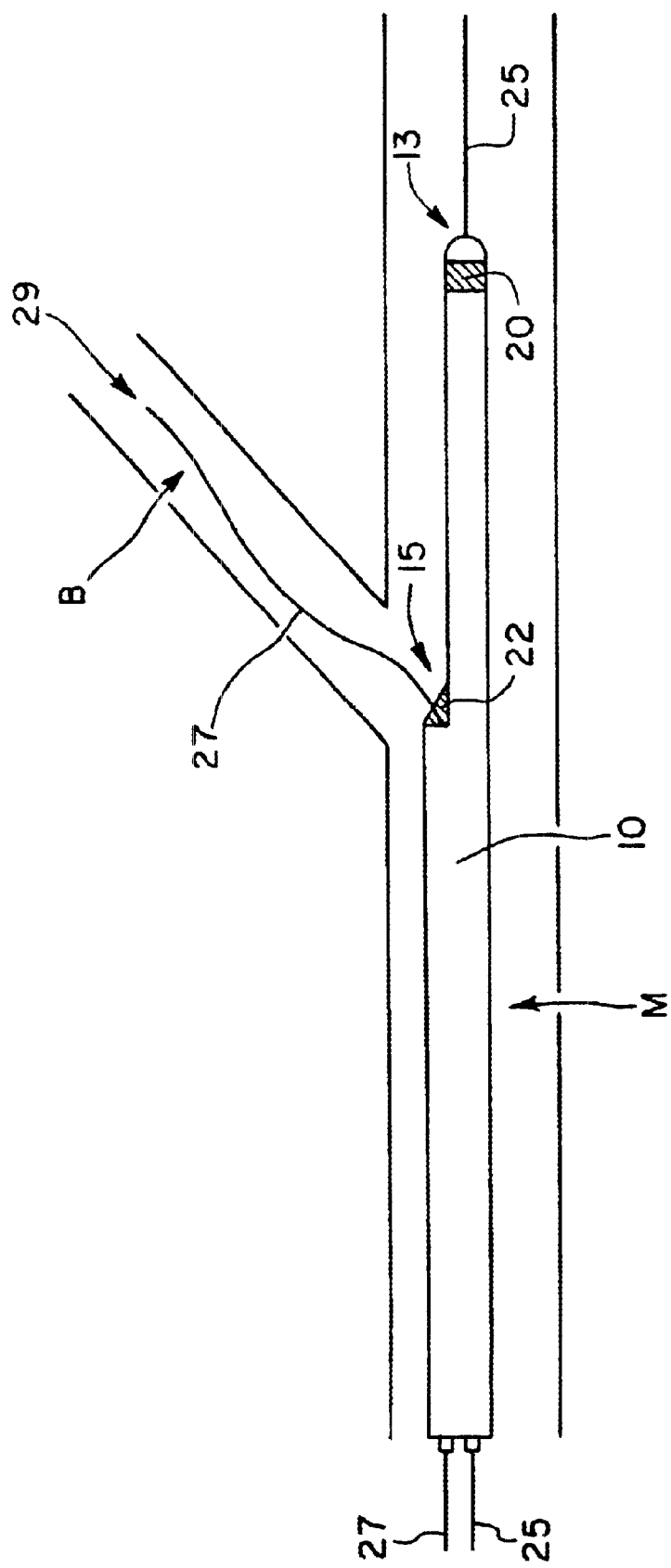
FIG. 5 is an illustration of a second guidewire advanced through the second lumen of the introducer with the distal end of the second guidewire positioned in the branch vessel.
Figure 6:
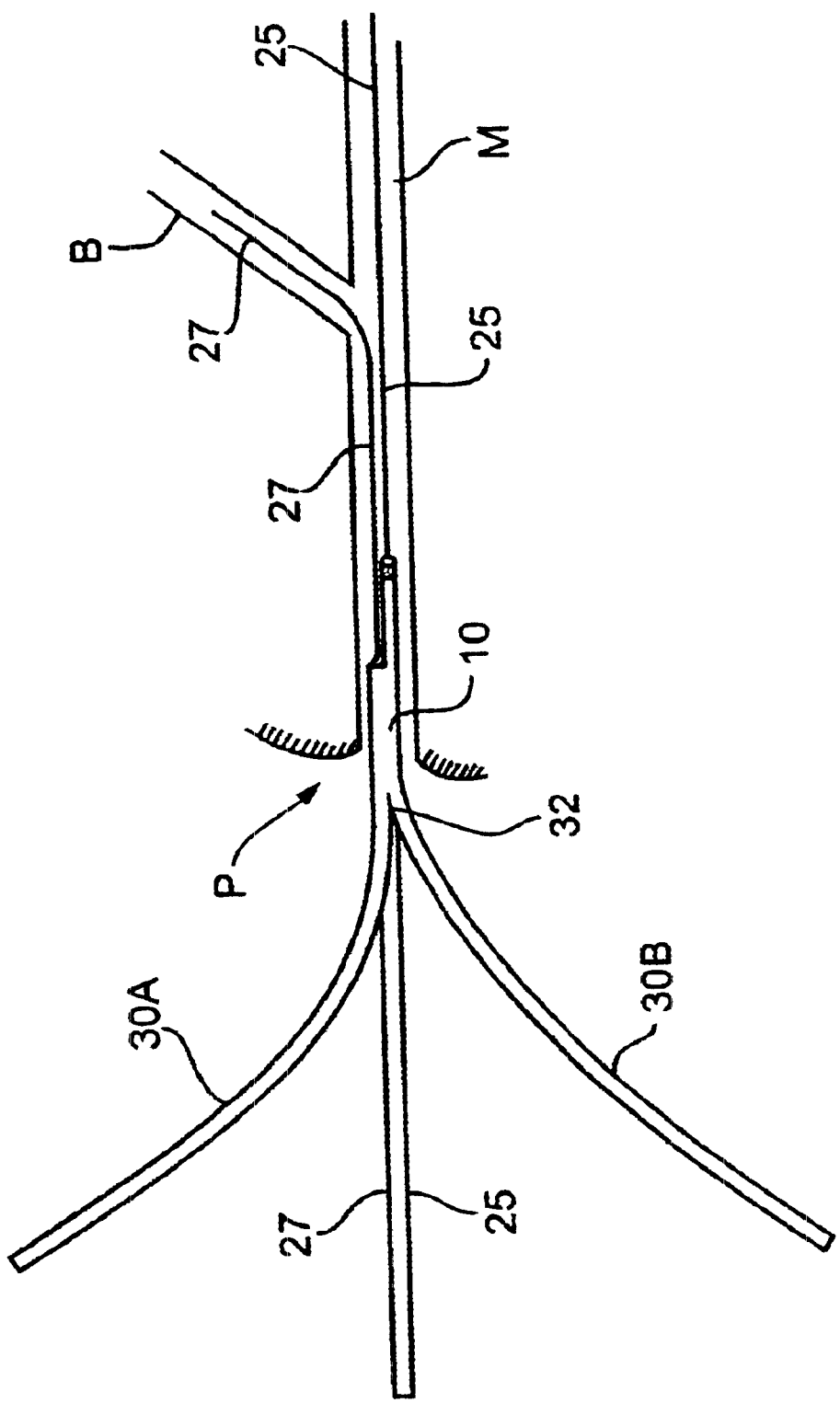
FIG. 6 is an illustration of the removal of the present guidewire introducer, showing the proximal end of the introducer separated into a plurality of longitudinally extending sections.
Figure 7:
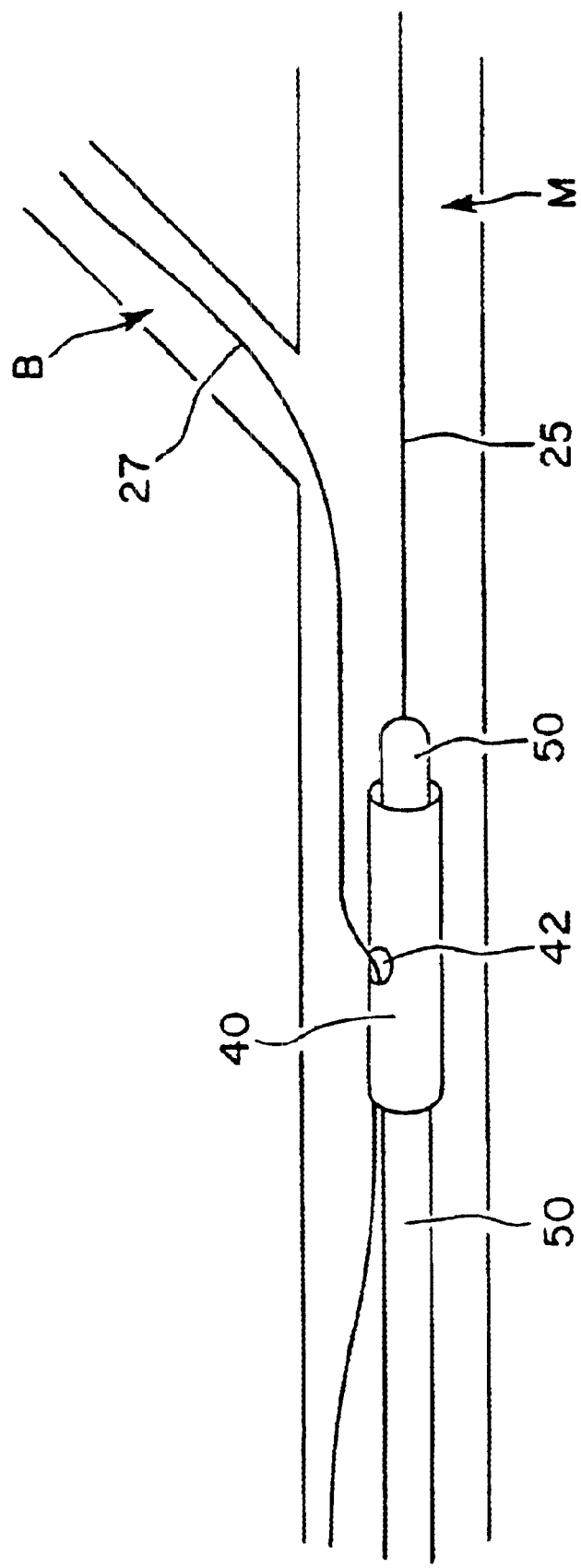
FIG. 7 is an illustration of a main stent being advanced into the bifurcation by a first catheter which is advanced over the first guidewire, showing the second guidewire passing through a side opening in the main stent and into the branch vessel.
Figure 8:
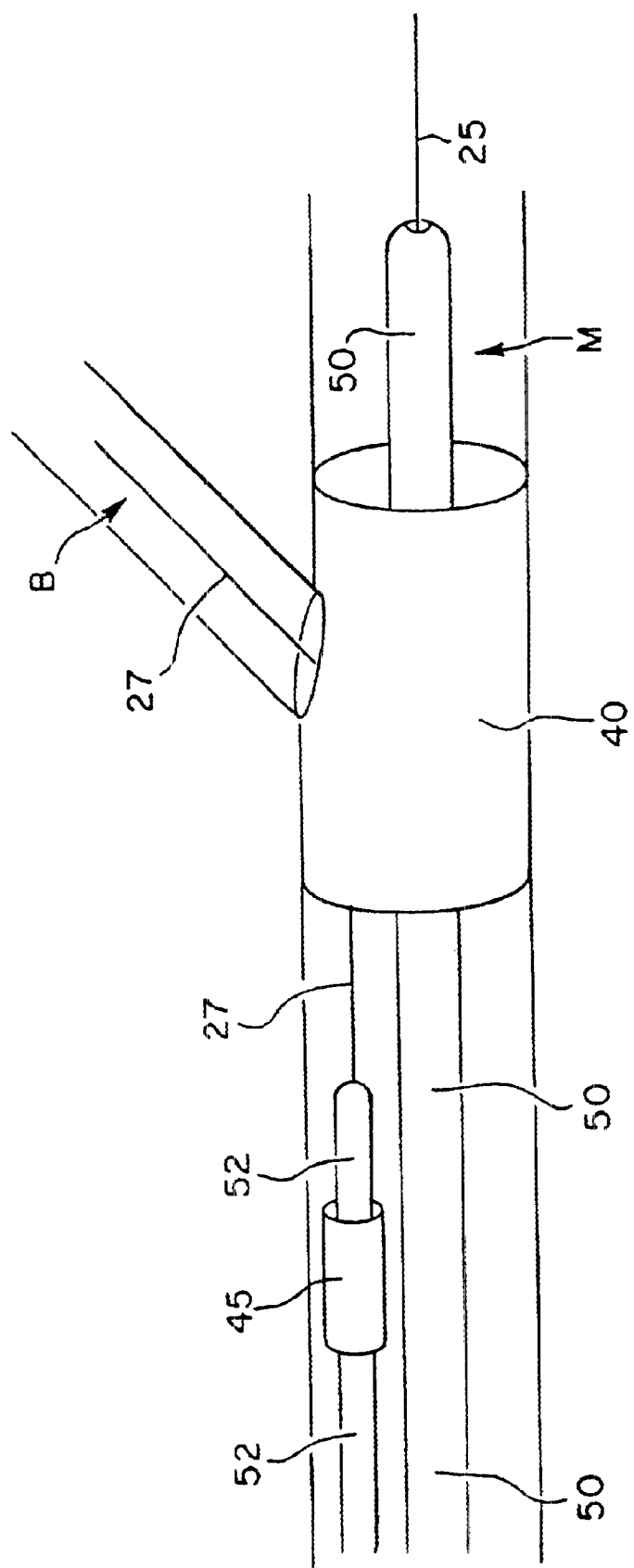
FIG. 8 is an illustration of the main stent deployed in the bifurcation, showing a branch stent being advanced into the bifurcation by a second catheter which is advanced over the second guidewire.
Figure 9:
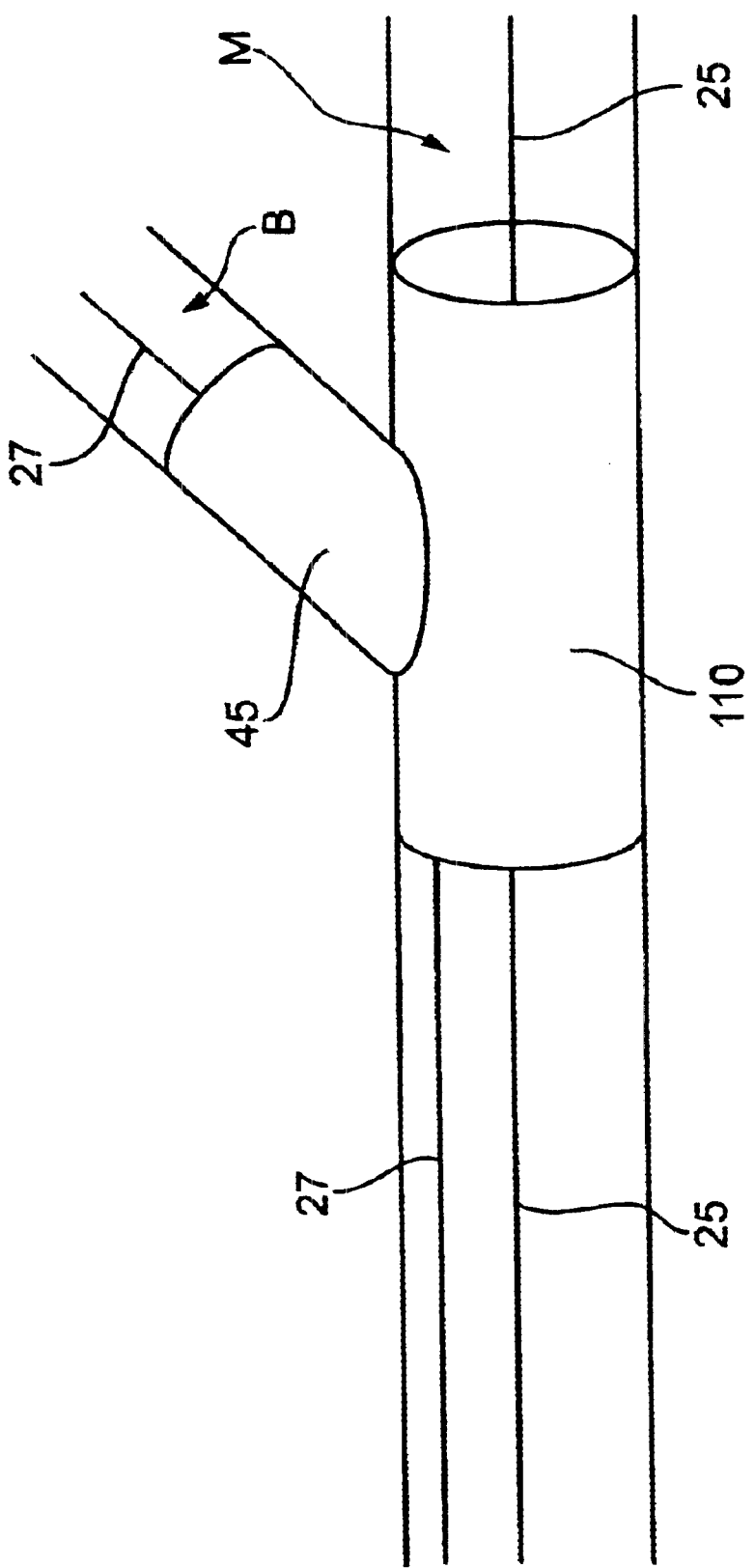
FIG. 9 is an illustration of the deployment of main and branch stent at the bifurcation with the first and second catheters removed.

FIGS. 3 to 5 show sequential steps involved in inserting first guidewire 25 into a main vessel and in inserting second guidewire 27 into a branch vessel using the present guidewire introducer 10. FIG. 6 shows the additional preferred step of removing guidewire introducer 10, leaving the first and second guidewires in position at the vessel bifurcation. FIGS. 7 to 9 show optional steps which may be carried out after the first and second guidewires have been positioned in the bifurcation and the guidewire introducer has been removed.

The preferred method of inserting a main guidewire into a main vessel and a branch guidewire into a branch vessel at an intersection of a main and branch vessel is illustrated in FIGS. 3 to 5, as follows. Referring to FIG. 3, first guidewire 25 is advanced through main vessel M such that a distal end 26 of first guidewire 25 is positioned past the intersection of main M and branch B vessels.

Referring to FIG. 4, dual lumen guidewire introducer 10 is then advanced through main vessel M over first guidewire 25, with first guidewire 25 being received within first lumen 12 of dual lumen guidewire introducer 10. By viewing the position of radiopaque marker 22 under fluoroscopy, the surgeon is able to easily position distal end opening 15 of lumen 14 at the bifurcation. As such, dual lumen guidewire introducer 10 is preferably positioned such that distal end 13 of first lumen 12 is disposed distally past the bifurcation of the main M and branch B vessels.

Radiopaque marker 20 enables the surgeon to determine that the distal end opening 13 of lumen 12 has moved distally past the bifurcation.

Referring to FIG. 5, the second guidewire 27 is then advanced through second lumen 14 such that a distal end 29 of second guidewire 27 passes out of the distal end opening 15 of second lumen 14 and into branch vessel B.

Thereafter, guidewire introducer 10 is then removed, leaving first guidewire 25 in main vessel M (with its distal end 26 disposed past the intersection of the main and branch vessels), and second guidewire 27 in branch vessel B. In one embodiment, introducer 10 is removed while maintaining first guidewire 26 in the main vessel so that distal end 26 is disposed past or distal to the bifurcation or vessel intersection. Similarly, in one embodiment, the introducer is removed while maintaining second guidewire 27 in the branch vessel so that distal end 29 is disposed past or distal to the vessel intersection.

FIG. 6 shows an optional feature of guidewire introducer 10 as the introducer is removed from a patient, as follows. In a preferred aspect, guidewire introducer 10 is made of a tear away material, formed as a plurality of longitudinally extending sections 30A and 30B, held together by tear-away seams 32. Seams 32 may include seam 18 shown in FIG. 1B. (It is to be understood that introducer 10 may be formed of more than two longitudinally extending sections 30, and that the present invention is not limited to any particular number of such sections 30. Here, two sections 30A and 30B are shown simply for ease of illustration). In accordance with the preferred method, introducer 10 may be removed by an operator such that introducer 10 is peeled apart into separated sections 30A and 30B, while the operator holds onto guidewires 25 and 27 such that these guidewires do not move as the introducer is removed.

Advantages of separating guidewire introducer 10 into a plurality of separate sections include providing surgeon access to guidewires 25 and 27 at a location adjacent the surface of patient P, without having to fully remove the introducer by fully pulling it proximally over the entire lengths of guidewires 25 and 27.

As such, the surgeon is free to operate with shorter wires, by accessing the guidewires 25 and 27 at positions closer to the body of the patient, (thus avoiding the need for longer exchange-type wires).

FIGS. 7 to 9 show optional stent insertion techniques which may be carried out after guidewires 25 and 27 have been inserted into position through the bifurcation and after guidewire introducer 10 has been removed.

Referring to FIG. 7, a main stent 40 having a side opening 42 can be advanced by a first catheter 50 over first guidewire 25 (with second guidewire 27 passing through side opening 42 as shown). As shown in FIG. 8, main stent 40 may then be deployed by first catheter 50 at the vessel bifurcation with its side opening 42 aligned with the ostium of branch vessel B. Should it be desired, a branch stent 45 may be deployed at the bifurcation by advancing branch stent 45 with a second catheter 52 over second guidewire 27, to the position shown in FIG. 9, (where it may be fully deployed by catheter 52, with first and second catheters 50, 52 then being removed.

The various optional aspects and uses of the present invention following guidewire placement as shown in FIGS. 7 to 9 are more fully illustrated in copending U.S. patent application Ser. Nos. 08/744,022 filed Nov. 4, 1996, now abandoned; Ser. No. 08/935,383 filed Sep. 23, 1997; Ser. No. 09/007,265 filed Jan. 14, 1998; U.S. Provisional Patent Application No. 60/088,301 filed Jun. 5, 1998; PCT Patent Application No. PCT/US99/00835 filed Jan. 14, 1999; U.S. patent application Ser. No. 09/325,996 filed Jun. 4, 1999, and Ser. No. 09/455,299 filed Dec. 6, 1999, the disclosures of which are incorporated herein by reference in their entirety for all purposes.

Optional balloons (not shown) on the distal ends of first and second catheters 50, 52 may be used to deploy main stent 40 and branch stent 45, respectively.

In optional aspects, radially expandable portions (not shown) which may be deployed to extend laterally outwards from the edges of side opening 42 may be included to anchor side opening 42 in registry with the ostium of branch vessel B. A full description of such radially expandable portions (which push against the walls of branch vessel B), is found in the Published PCT Patent Application WO 99/00835, filed Jan. 14, 1998, incorporated herein by reference in its entirety.

Optionally as well, branch stent 45 may further comprise a contact portion (not shown) which remains disposed within side opening 40 after stents 40 and 45 have been deployed, thereby securing the proximal end of stent 45 to side opening 42 of stent 40, thereby fully covering the bifurcation. Such a contacting portion is further described in copending PCT Patent Application WO 99/00835, filed Jan. 14, 1998.

Figure 10:
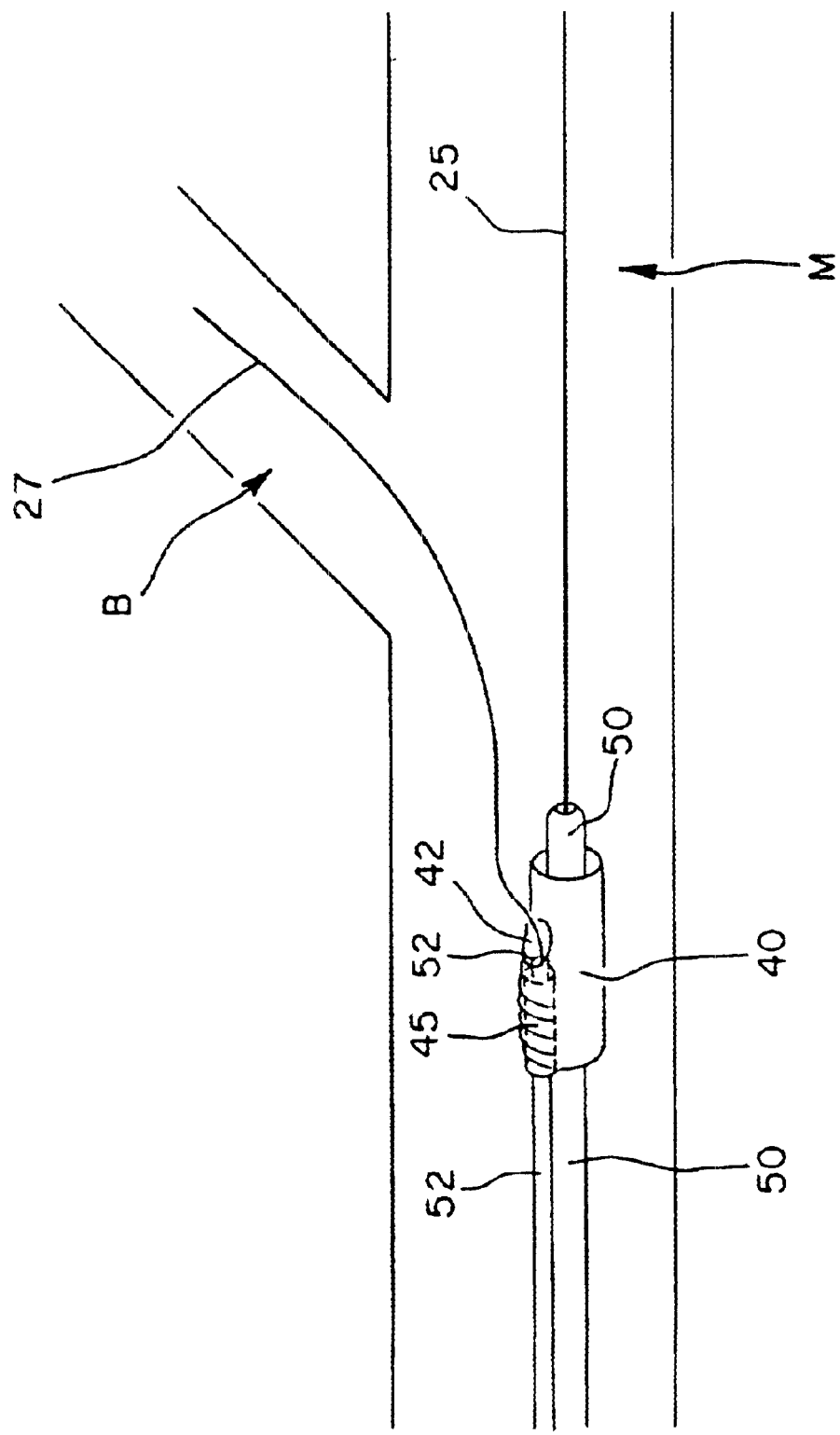
FIG. 10 shows an alternate method of simultaneously advancing main and branch stents into a bifurcation over the first and second guidewires.

FIG. 10 shows an alternate method of inserting main and branch stents 40 and 45 into the bifurcation over first guidewire 25 and second guidewire 27 wherein main stent 40 and branch stent 45 are inserted into the bifurcation together. As such, the method of simultaneously inserting main and branch stent 40, 45 illustrated in FIG. 10 can be used instead of the method of sequential insertion of main stent 40 and branch stent 45 as illustrated in FIGS. 7 and 8, yet still achieve the same final result as is shown in FIG. 9. Specifically, as shown in FIG. 10, branch stent 45 can first be crimped within main stent 40, such that the main and branch stents 40, 45 can be inserted together as an assembled unit into the bifurcation. After main stent 40 has been at least partially deployed by catheter 50, (for example, by being expanded by a balloon at the distal end of catheter 50), branch stent 45 will no longer be crimped in a fixed position within main stent 40. As such, branch stent 45 will be released from the crimped hold of main stent 40 such that catheter 52 may be advanced distally so as to deploy branch stent 45 in the branch vessel through a side opening 42 in main stent 40.

In optional preferred aspects shown in FIGS. 11 to 15, radiopaque markers are provided on opposite sides of the introducer shaft at a location proximal the distal end of the second lumen. Such radiopaque markers may be advantageously used to assist the surgeon in aligning a side opening in a main stent with the ostium of a branch vessel, as follows.

Figure 11:
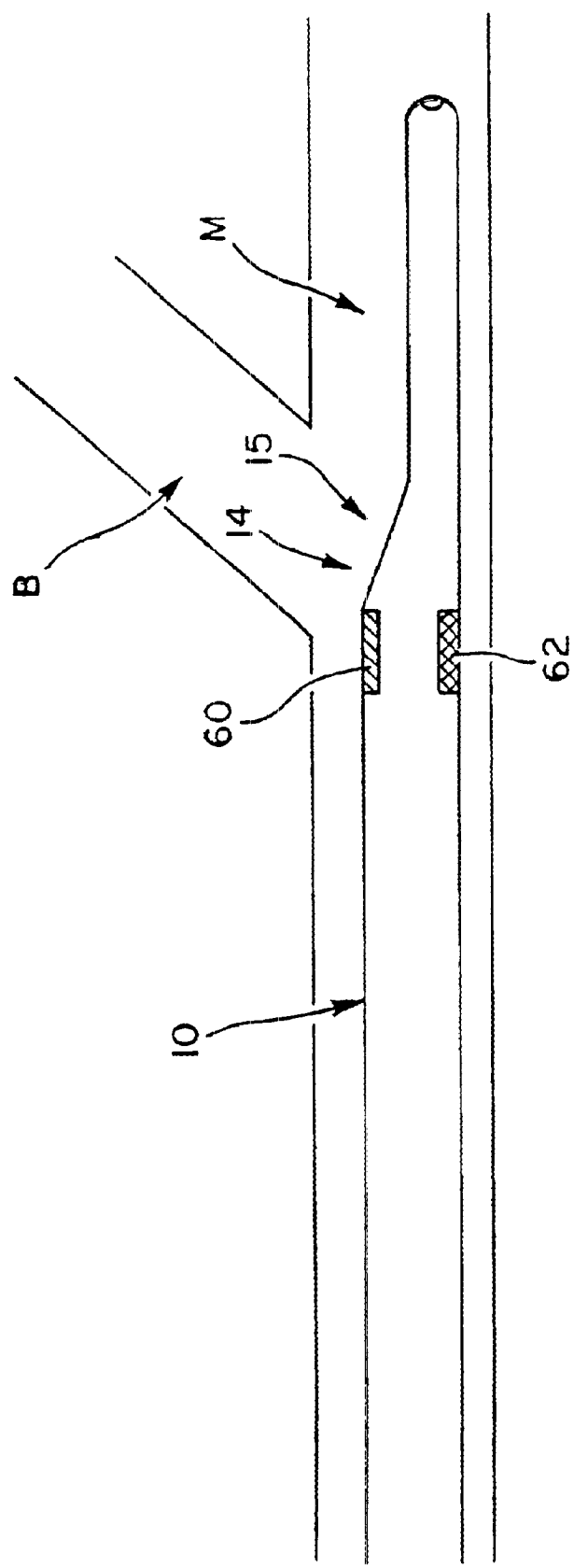
FIG. 11 is an illustration of a dual lumen guidewire introducer with radiopaque markers disposed on opposite sides of the introducer shaft at a location proximal the distal end of the second lumen.

Referring to FIG. 11, radiopaque markers 60 and 62 are positioned on opposite sides of introducer 10 adjacent the distal end 15 of second lumen 14. When viewed radioscopically, the operator will be able to see radiopaque markers 60 and 62. Preferably, radiopaque markers 60 and 62 will be made of different material such that each of markers 60 and 62 will appear different in the radioscopic image viewed by the surgeon. For example, one of markers 60 and 62 can be made from gold while the other is made from platinum, offering varying degrees of radiopacity for each marker. It will be appreciated by those skilled in the art that different materials, including different metals, also may be used within the scope of the present invention.

Figure 12B:
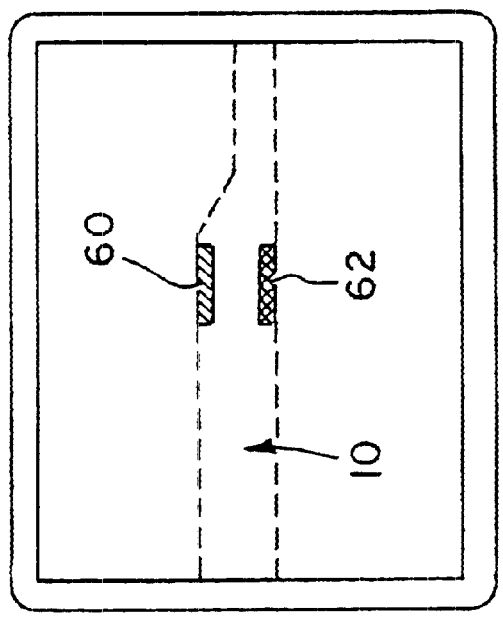
FIG. 12B is an on-screen radiopaque image corresponding to FIG. 12A.
Figure 12A:
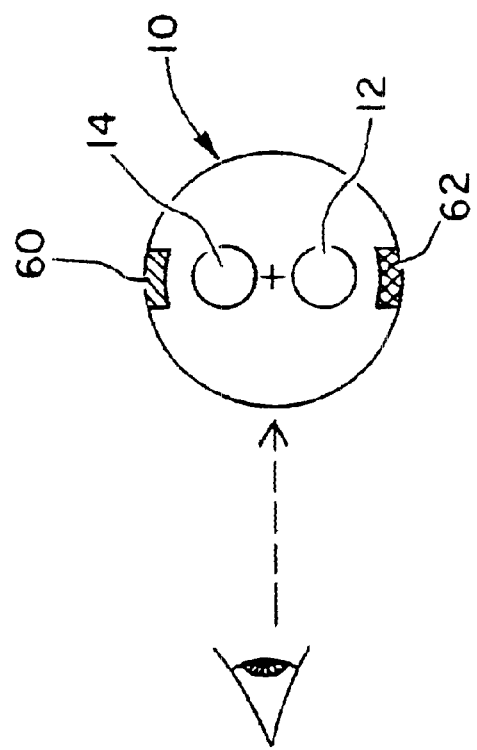
FIG. 12A is an end view of the system of FIG. 11 as viewed by an operator.
Figure 13B:
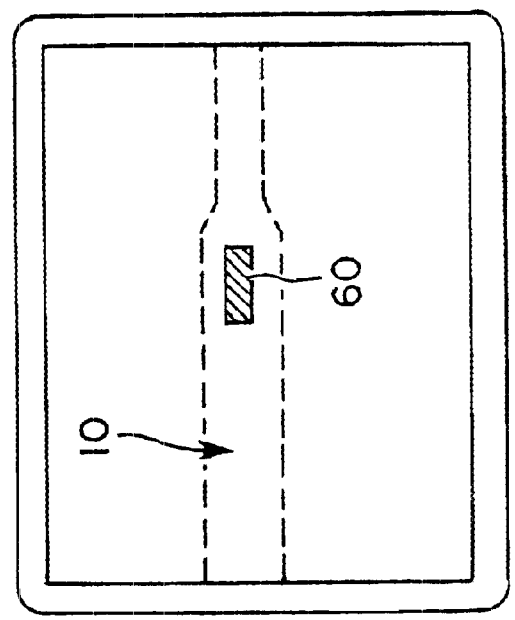
FIG. 13B is an on-screen radiopaque image corresponding to FIG. 13A.
Figure 13A:
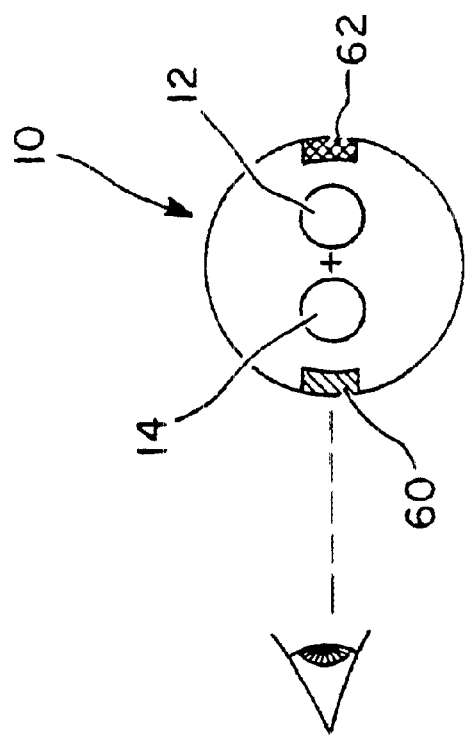
FIG. 13A is another end view of the system of FIG. 11 as viewed by an operator, rotated from the position shown in FIG. 12A.
Figure 14B:
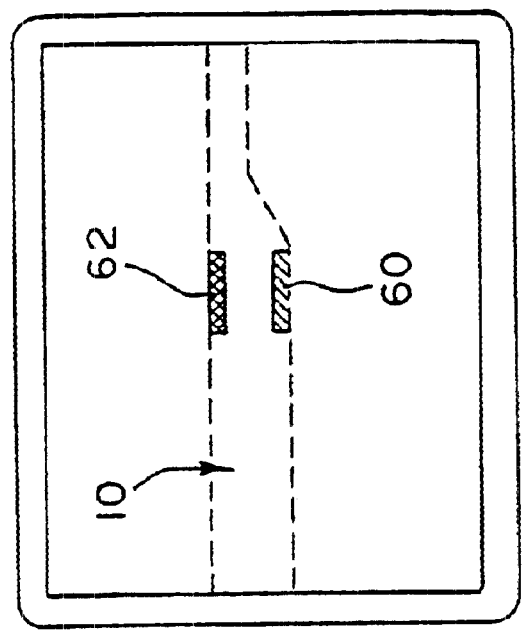
FIG. 14B is an on-screen radiopaque image corresponding to FIG. 14A.
Figure 14A:
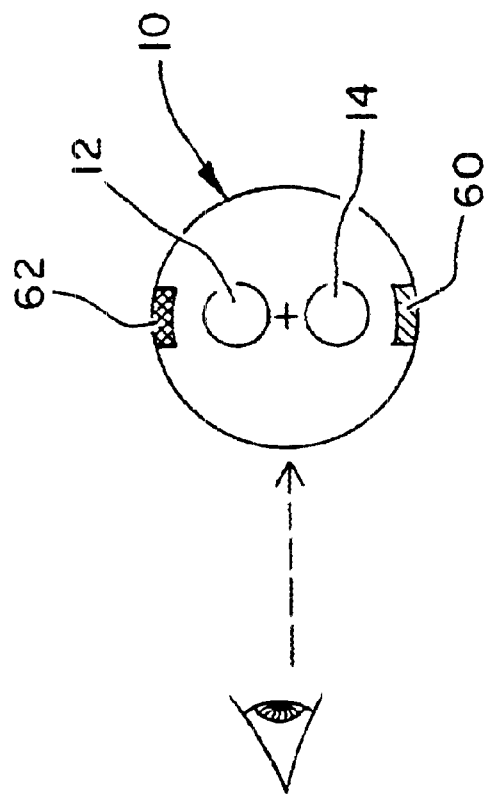
FIG. 14A is an end view of the system of FIG. 11 as viewed by an operator, rotated from the positions shown in both FIGS. 12A and 13A.

As can be seen in FIG. 12A, an operator radioscopically viewing introducer 10 from the angle shown will see the image of markers 60 and 62 as shown in the onscreen display of FIG. 12B. (Introducer 10 is shown in phantom for reference since as it is not viewable by the operator radioscopically). FIGS. 13A to 14B show similar images as introducer 10 is rotated.

Figure 15:
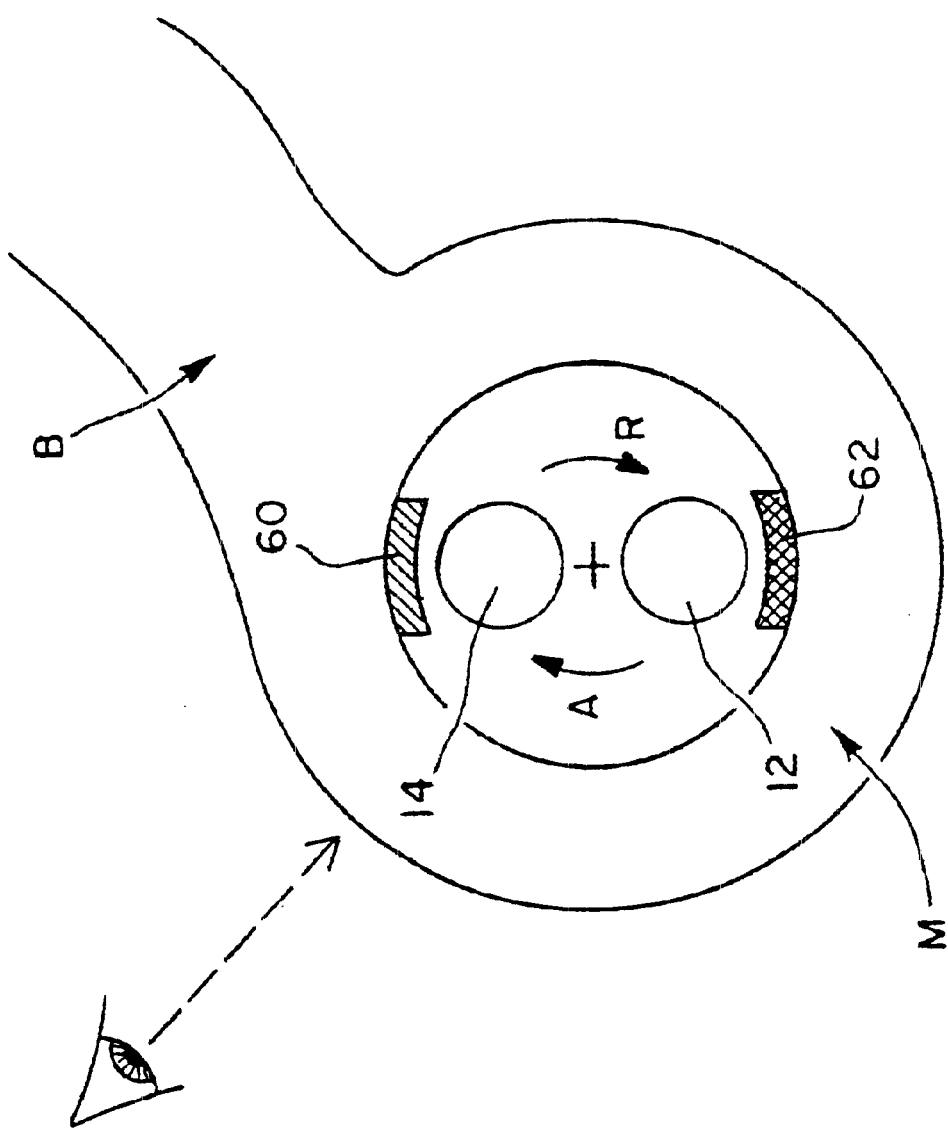
FIG. 15 is an end view of the system of FIG. 11 as viewed by an operator, as shown positioned at a vessel bifurcation.

An advantage of markers 60 and 62 having differing degrees of radiopacity is that, as shown in FIG. 15, introducer 10 can be rotated in direction R such that marker 60 can easily be aligned with the mouth of branch vessel B. Specifically, when aligned, an operator viewing introducer 10 from an angle perpendicular to the angle at which branch vessel B extends from the main vessel M (as shown) will see a maximum separation between markers 60 and 62 (which would be achieved after marker 60 has been aligned with the mouth of branch vessel B, as explained).

In an exemplary aspect of the present invention, introducer 10 has a diameter in the range of about 6 French to about 8 French.

In one aspect of the present invention, first and second guidewires 25 and 27 have diameters in the range of about 0.014 inches to about 0.035 inches, and first and second lumens 12 and 14 have diameters in the range of about 0.016 inches to about 0.038 inches. In a particular aspect of the present invention, the distance between the distal openings of the first and second lumens is in the range of about 0.039 inches to about 2.5 inches.

Figure 16:
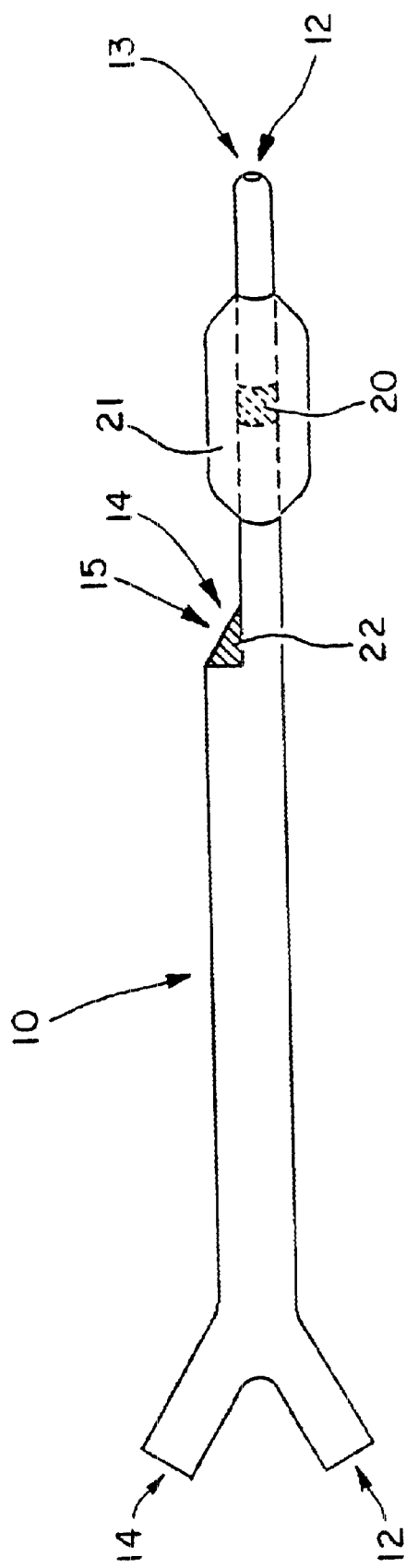
FIG. 16 is an illustration of a dual lumen guidewire introducer having a distal balloon.

Referring to FIG. 16, in one embodiment, a balloon 21 is positioned at the distal end of introducer 10. Balloon 21 may be inflated to pre-dilate main vessel M either before, after, or concurrently with, second guidewire 27 being inserted into branch vessel B. In one embodiment, balloon 21 is inflated to flatten or otherwise compress plaque or other material (not shown), such as at a vessel stenosis, against the wall of main vessel M. Introducer 10, in an embodiment, further includes an inflation lumen (not shown in FIG. 16) coupled to balloon 21 for providing an inflation fluid to inflate balloon 21.

In another embodiment, lumen 14 is of sufficient size to receive a second balloon therethrough. In an embodiment, a catheter (not shown in FIG. 16) having the second balloon proximate a distal end thereof is inserted into lumen 14. The second balloon insertion may occur before, after or concurrent with second guidewire 27 introduction. The second balloon may be inflated to encourage plaque or other obstructions against the vessel wall of main vessel M and/or branch vessel B. In still another embodiment, both the second balloon and balloon 21 are inflated to encourage plaque or other vessel obstructions against the vessel walls. In a particular embodiment, the second balloon and balloon 21 are used in a "kissing balloon" technique known to those skilled in the art. Such a technique may be used at or near the intersection of the branch and main vessels. For example, in one embodiment, the second balloon is introduced into branch vessel B and balloon 21 is introduced into main vessel M. Both the second balloon and balloon 21 are inflated about the intersection of the main and branch vessels. Use of introducer 10 in conjunction with the kissing balloon technique helps facilitates the proper alignment of the balloons in the vessel(s).

The present invention also comprises kits including the apparatus of the present invention with instructions for use setting forth any of the herein disclosed methods for use.

The invention has now been described in detail for purposes of clarity and understanding. However, it will be appreciated that certain changes and modifications may be practiced within the scope of the appended claims. By way of example, the present invention will find use in a variety of bifurcated vessels, and is not limited to a main vessel—branch vessel intersection.

What is claimed is:

1. A system for introducing a guidewire into a branch vessel, said system comprising:
   a guidewire introducer having a first lumen, and a second lumen adjacent said first lumen, each of said first and second lumens having a distal opening,
   wherein said second lumen comprises a deflector located proximate said second lumen distal opening, said deflector configured to deflect a guidewire end through said second lumen distal opening;
   a first marker having a first radiopacity, said first marker disposed on a first side of said introducer adjacent said second distal opening; and
   a second marker having a second radiopacity, said second marker disposed on a second side of said introducer adjacent said second distal opening, wherein said first side is opposite said second side, and wherein said first radiopacity is different from said second radiopacity.

2. The system as in claim 1 wherein said second lumen comprises a longitudinal axis, and wherein said deflector is positioned at a non-parallel angle relative to said longitudinal axis.

3. The system as in claim 2 wherein said non-parallel angle is about forty five (45) degrees.

4. The system as in claim 1 further comprising:
   a first guidewire adapted to receive said first lumen thereover; and
   a first catheter having a balloon disposed proximate a first catheter distal end, said first catheter adapted to be inserted over said first guidewire into a main vessel after removal of said guidewire introducer.

5. The system as in claim 1 further comprising:
   a second guidewire adapted to be slidably received by said second lumen; and
   a second catheter having a balloon disposed proximate a second catheter distal end, said second catheter adapted to be inserted over said second guidewire into a main vessel after removal of said guidewire introducer.

6. The system as in claim 1 wherein the distal opening of the first lumen is disposed at a more distal location along the guidewire introducer with respect to the distal opening of the second lumen.

7. The system as in claim 2 wherein said second lumen distal opening is positioned at a non-parallel angle relative to said longitudinal axis.

8. The system as in claim 1, wherein the difference in said first and second radiopacities is due to differences in thickness of said first and second radiopaque markers.

9. The system as in claim 1, wherein the difference in said first and second radiopacities is due to differences in size of said first and second radiopaque markers.

10. The system as in claim 1, wherein the difference in said first and second radiopacities is due to differences in material of said first and second radiopaque markers.

11. The system as in claim 1 further comprising:
    a second guidewire adapted to be slidably received by said second lumen; and a second catheter having a balloon disposed proximate a second catheter distal end, said second catheter adapted to be inserted over said second guidewire into a main vessel after removal of said guidewire introducer.

12. A method of introducing a branch vessel guidewire, said method comprising:

inserting a first guidewire into a main vessel;

advancing a guidewire introducer through said main vessel over said first guidewire, said guidewire introducer having a first lumen that slidably engages said first guidewire;

positioning the guidewire introducer such that a distal end of the first lumen is disposed past a bifurcation of the main and branch vessels, and a radiopaque marker on the guidewire introducer is proximate said bifurcation; and thereafter advancing a second guidewire through a second guidewire introducer lumen adjacent said first lumen, said second guidewire introducer lumen having an opening proximate a distal end of said second lumen.

13. The method of claim 12, further comprising:

removing the guidewire introducer from the main vessel;

inserting a first catheter into said main vessel; and expanding a first balloon on said catheter when said balloon is proximate said bifurcation.

14. The method of claim 13, further comprising:

inserting a second catheter into a branch vessel; and expanding a second balloon on said second catheter.

15. The method of claim 14 wherein said expanding a balloon on said second catheter comprises expanding said second catheter balloon when said second catheter balloon is at least partially disposed in said branch vessel.

16. The method as in claim 14 wherein said expanding said first and second balloons comprises a kissing balloon technique.

17. The method as in claim 14 wherein said expanding said first and second balloons comprises expanding said first balloon in said main vessel and expanding said second balloon in said branch vessel.

18. The method of claim 12, wherein said second lumen has a deflector and wherein said advancing the second guidewire comprises deflecting said second guidewire with said deflector so that an end of said second guidewire advances into said branch vessel.

19. A system for introducing a guidewire into a branch vessel, said system comprising:

a guidewire introducer having first and second lumens, each of said first and second lumens having a distal opening, a first marker having a first radiopacity, said first marker disposed adjacent said first distal opening; and a second marker having a second radiopacity, said second marker disposed adjacent said second distal opening, wherein said first radiopacity is different from said second radiopacity.

20. The system as in claim 1 further comprising:

a first guidewire adapted to receive said first lumen thereover; and a first catheter having a balloon disposed proximate a first catheter distal end, said first catheter adapted to be inserted over said first guidewire into a main vessel after removal of said guidewire introducer.

21. The system as in claim 19 wherein the distal opening of the first lumen is disposed at a more distal location along the guidewire introducer with respect to the distal opening of the second lumen.

* * * * *